United States Patent [19]
Sowden et al.

[11] Patent Number: 5,417,693
[45] Date of Patent: May 23, 1995

[54] INSTRUMENTATION FOR PREPARING THE FEMUR FOR AN ARTIFICIAL KNEE IMPLANT AND FOR POSITIONING THE FEMORAL COMPONENT OF THE IMPLANT

[75] Inventors: Bjorn K. Sowden, North Anston; John Egan, Todwick, both of Great Britain

[73] Assignee: Minnesota Mining and Manufacturing Company, St. Paul, Minn.

[21] Appl. No.: 78,913

[22] Filed: Jun. 16, 1993

[30] Foreign Application Priority Data

Jun. 17, 1992 [GB] United Kingdom .............. 9212809.9
Jun. 17, 1992 [GB] United Kingdom .............. 9212810.7

[51] Int. Cl.$^6$ ............................................. A61B 17/56
[52] U.S. Cl. ................................. 606/85; 606/99; 623/20; 269/3; 269/6; 269/234; 269/238
[58] Field of Search ............... 606/99, 100, 104, 79, 606/80, 81, 84, 85; 623/20; 29/275; 81/90.1, 90.2; 269/238, 234, 3, 6

[56] References Cited

U.S. PATENT DOCUMENTS

| | | | |
|---|---|---|---|
| D. 230,095 | 1/1974 | Rylee . | |
| D. 230,097 | 1/1974 | Rylee . | |
| 3,857,389 | 12/1974 | Amstutz . | |
| 3,869,731 | 3/1975 | Waugh et al. | 623/20 |
| 4,081,866 | 4/1978 | Upshaw et al. . | |
| 4,246,895 | 1/1981 | Rehder . | |
| 4,601,289 | 7/1986 | Chiarizzio et al. . | |
| 4,664,212 | 5/1987 | Nagatsuka et al. . | |
| 4,721,104 | 1/1988 | Kaufman et al. . | |
| 4,869,663 | 1/1990 | Vanderwalls | 606/79 |
| 5,021,055 | 6/1991 | Burkinshaw et al. | 606/82 |
| 5,059,196 | 10/1991 | Coates | 606/99 |
| 5,069,432 | 12/1991 | Reising | 269/3 |
| 5,089,004 | 2/1992 | Averill et al. | 606/85 |
| 5,096,169 | 3/1992 | Behnke | 269/3 |
| 5,100,409 | 3/1992 | Coates et al. | 606/88 |
| 5,124,106 | 6/1992 | Morr et al. | 264/221 |
| 5,129,908 | 7/1992 | Petersen | 606/88 |
| 5,169,401 | 12/1992 | Lester et al. | 606/79 |

FOREIGN PATENT DOCUMENTS

| | | |
|---|---|---|
| 0194014 | 9/1986 | European Pat. Off. . |
| 0380451 | 8/1990 | European Pat. Off. . |
| 0441059 | 8/1991 | European Pat. Off. . |
| 1570863 | 7/1980 | United Kingdom . |

OTHER PUBLICATIONS

Page entitled "Assessment of Fit" Author unknown, Publication unknown, Date unknown.

*Primary Examiner*—Stephen C. Pellegrino
*Assistant Examiner*—Guy V. Tucker
*Attorney, Agent, or Firm*—Gary L. Griswold; Walter N. Kirn; Stephen W. Bauer

[57] ABSTRACT

An impactor/extractor holder for a femoral trial and/or a knee implant to hold and guide those items onto the resected end of a femur. The impactor/extractor holder comprises two opposed clamping arms for gripping the opposite outer edges of the trial and/or implant, and an abutment table movable relative to the clamping arms so as to be capable of being advanced against the outer surface of the trial and/or implant after the sides have been clamped by the clamping jaws. The abutment table has a cushioning surface for contacting the trial and/or implant which is adapted not to damage the outer surface of the implant or trail. A threaded mechanism is provided for moving the abutment table relative to the clamping jaws to advance the cushioning surface of the abutment table against the outer surface of the implant or the trial to securely and rigidly lock the trial or implant on the impactor/extractor holder. A trial rasp is also disclosed.

41 Claims, 4 Drawing Sheets

INSTRUMENTATION FOR PREPARING THE FEMUR FOR AN ARTIFICIAL KNEE IMPLANT AND FOR POSITIONING THE FEMORAL COMPONENT OF THE IMPLANT This invention relates generally to instrumentation and methods for preparing the distal end of the femur for the femoral component of an artificial knee implant, and for positioning the femoral component of the implant on the prepared distal end of the femur.

BACKGROUND OF THE INVENTION

In the replacement of a knee by an artificial joint, it is necessary to shape the distal end of the femur by making a number of cuts through the condyles to precisely receive the femoral component of the replacement joint. The femoral component is of hollow bowl or generally "C" shape, and it has a generally concave inner surface designed to fit with the cut end of the femur. The cuts which are made may need some slight adjustments in order to ensure that the implant will ultimately fit very closely over the resected bone with what is known as an interference fit, that is, a tight fit such that the implant could be, for example, up to 2% smaller than the bone to which it is to be fitted. In this way the implant will be a tight fit on the bone and there will be no chance of the implant rocking on the bone and so leading to failure. Also any gaps or deviations greater than this are counterproductive with respect to bone incorporation into the surfaces of the implant.

When preparing the femur to receive its respective component of the artificial knee joint, the various cuts are made using a guide which should result in a final reasonably accurate shape. See, for example, the guide described in co-assigned British Patent Application No. 9213766.0. In particular, those condylar cuts which are across the axis of the bone and which take most of the load, do not contribute much to the interference fit of the implant and are angled to optimize load distribution between the bone and the implant whilst also ensuring bone incorporation. However, those condylar cuts which run parallel or close to parallel to the axis of the bone do need further preparation to ensure the final accurate interference fit and ideally this is achieved by making the appropriate cuts such that the bone is very slightly over size and then subjecting it to a final rasping action to achieve the exact size required.

Once the cuts have been made it is usual for a femoral trial, which is of the same shape and size as the final knee implant, to be fitted over the resected femur to check the correct sizing and positioning of the cuts. Thereafter once the trial has been removed, the final implant has to be manoeuvred into place taking care not to substantially alter the cut surfaces of the bone or damage the articulation surface of the artificial joint.

For these reasons it is desirable to have some sort of impactor/extractor holder which can grasp the trial and the final implant and help one in positioning them on the cut end of the femur. The holder must be substantial, since it will often be necessary to hammer it to force both the trial and the implant into final position. Equally however the holder must not damage the highly polished articulation surface of the final implant. Further, there must be very secure attachment between the holder and either the implant or the trial, so that they become, in effect, one and the same whilst the trial and/or implant are being manoeuvred into position on the cut femur.

U.S. Pat. No. 5,059,196 (Coates) shows a femoral prosthesis holder/driver tool and method of implantation using same. That tool includes impact pads, and fingers that are spread to grip the internal wall adjacent the intercondylar notch opening. That patent asserts an advantage to having fingers which grip the internal walls of the prosthesis as being "minimal risk of trauma to the underlying tissue of the joint capsule, from contact with various components of the tool." It is, however, believed that with such internal fingers the posterior cruciate ligament may interfere with placement of the prosthesis.

SUMMARY OF THE INVENTION

This invention provides an impactor/extractor holder which has uses during the replacement of a knee by an artificial joint. In particular, the impactor/extractor holder of the invention is used for placing and/or extracting a femoral trial to check on the accurate shaping of the femur and for placing the actual knee implant in position on the femur. The impactor/extractor holder is also designed to be used with a novel trial rasp.

The impactor/extractor of the invention is particularly designed to engage the opposite outer edges of the femoral implant, trial or rasp and the curved outer surface of the implant, trial or rasp to securely hold and guide the implant, trial or rasp onto the resected end of a femur.

Generally, the impactor/extractor holder of the invention comprises two opposed clamping jaws movable toward one another for gripping the opposite outer edges of the trial and/or implant, and means for moving the clamping jaws relative to one another and adjustably maintaining the clamping jaws against relative outward movement. The impactor/extractor holder further comprises an abutment table movable relative to the clamping jaws so as to be capable of being advanced against the outer surface of the trial and/or implant after the sides have been clamped by the clamping jaws. The abutment table has a cushioning surface for contacting the trial and/or implant which will not damage the outer surface of the implant or trial. A suitable means is provided for moving the abutment table relative to the clamping jaws to advance the cushioning surface of the abutment table against the outer surface of the implant or the trial to securely and rigidly lock the trial or implant on the impactor/extractor holder.

Preferably, the means for moving the clamping jaws relative to one another and adjustably maintaining the clamping jaws against relative outward movement comprises first threaded adjustment means for moving the clamping jaws to grip the opposite edges of the trial or implant; and the means for moving the abutment table comprises second threaded adjustment means for adjustably moving the cushioning surface of the abutment table relative to the clamping jaws to securely and rigidly lock the implant or trial on the holder.

Accordingly, in an impactor/extractor holder according to the invention, one brings the clamping jaws toward one another to clamp the opposite outer edges of the femoral trial, implant or rasp, and thereafter one advances the abutment means to contact the outer surface of the trial or the articulation surface of the implant, so as to give a kind of three point contact which thereafter fixes the implant or trial relative the holder very rigidly indeed. The mechanical advantage of the clamping arrangement should be such as to ensure that the back pressure from the locking is sufficient to prevent loosening of the grip during manoeuvering of the trial or implant once the abutment member has gripped the implant.

Such a holder can be fixed very rigidly to the trial and/or implant and so in effect become one with it. It then becomes possible to manoeuvre the trial and/or implant into position quite accurately since the holder can be considerably larger than the trial or implant and therefore easily held and guided. In addition, the holder should be of substantial construction so that if necessary it can be hammered or the like to force the trial or implant into position on the end of the cut femur. Also the design of the holder should be such that any hammering forces are transmitted directly to the trial or implant.

According to the preferred embodiment of the invention it is desirable that both the clamping adjustment and the abutment adjustment be infinitely variable so that they can fit with a range of sizes of implants and/or trials. This can, for example, be achieved by means of screw thread adjustment for controlling the clamping action and the abutment action.

Also, preferably, the impactor/extractor holder is adapted for holding a trial or implant having opposed recesses in the opposite edges. For example, the clamping jaws may include locking projections sized and shaped to locate into opposed recesses on the trial and/or implant. Most preferably, the opposed recesses in the trial or implant have a generally rectangular cross section, and the locking projections have a generally rectangular cross section complementary to the recesses.

Preferably, the impactor/extractor holder has a main body having fulcra for the clamping jaws, and the clamping jaws comprise a pair of opposed two-armed levers pivotably mounted on the fulcra on the main body. Each lever comprises a clamping arm extending in one direction from its respective fulcrum, and an actuating arm extending from its respective clamping arm in the other direction from its respective fulcrum. The arrangement is such that, when the actuating arms are moved outwardly relative to the main body of the holder, the clamping arms are moved toward one another to clamp the opposite edges of the trial or implant. The first threaded adjustment means is adapted to move the actuating arms of the levers outwardly, thereby moving the clamping arms toward one another to clamp the opposite edges of the trial or implant.

Most preferably, the main body is generally elongate. The first threaded adjustment means comprises a rotatable member threadably mounted on the main body for rotation relative to the main body to move the rotatable member longitudinally along the main body. As the rotatable member is advanced along the main body in one direction, a generally conical or frustoconical surface on the rotatable member engages the actuating arms of the levers to move the actuating arms outwardly, thereby bringing the clamping arms toward one another. When the rotatable member is moved in the other direction along the main body, the conical or frustoconical surface of the rotatable member allows the actuating arms to move together, thereby allowing the clamping arms to move apart.

Also, most preferably, the main body has opposite ends, an outside threaded surface, and an inside threaded bore extending between its ends, with the abutment table and clamping arms being mounted adjacent one end of the main body. The rotatable member is threadably mounted on the outside threaded surface of the main body. The second threaded adjustment means includes a handle, adjacent the end of the main body opposite the clamping arms and abutment table, and a threaded shaft threadably received in the inside threaded bore of the main body. One end of the threaded shaft has the handle mounted thereon, and the other end of the threaded shaft is connected to the abutment table to move the abutment table relative to the clamping arms.

The abutment table is preferably so mounted on the main body as to allow movement in the direction of elongation of the main body without allowing rotation of the abutment table relative to the main body. The abutment table is so connected to the threaded shaft of the second threaded adjustment means as to move the abutment table in the direction of elongation of the main body without rotating the abutment table.

As noted above, the abutment table must have a cushioning surface such that the highly polished rolling surface of the knee joint is not damaged. This can be achieved by providing the abutment table with a flexible yet tough surface such that it can withstand hammering forces but yet not damage the highly polished surfaces of the implant. A suitable material is a synthetic plastics material, e.g. the composite resin material available under the trademark "TUFNOL" from Tufnol Limited, Birmingham, England, supported on a rigid metal backing.

The holder according to the invention is designed so that is can be easily cleaned and autoclaved, and where parts are screw threaded to one another the various components of the holder can be relatively easily dismantled to ensure thorough cleaning of all the threads.

In another aspect of the invention, the femoral trial comprises a novel trial rasp for preparing the femur for the femoral component of a knee joint prosthesis. Generally, the trial rasp of the invention comprises a generally C-shaped body having a concave side capable of being received over the end of the femur which has been prepared to receive the femoral component. The concave side of the body has a relatively smooth guiding surface along one end portion of the C-shaped body, and a rasping surface generally opposed to the guiding surface along the other end portion of the C-shaped body. The guiding surface is adapted to contact a prepared posterior surface of the femur which has been cut in a direction substantially parallel to the axis of the femur to guide the rasp relative to the posterior surface of the femur. The rasping surface is adapted to contact a prepared anterior surface of the femur, and to rasp the prepared anterior surface of the femur as the trial rasp is advanced over the end of the femur while the guiding surfaces engages the prepared posterior surface to guide the rasping surface in proper alignment relative to the femur.

Preferably, the rasping surface is not parallel to the guiding surface. For example, the rasping surface is oriented at an angle of approximately 5° relative to the guiding surface. The C-shaped body has outer free ends between which the femur is received along the concave side of the body. The rasping surface is oriented at an angle relative to the guiding surface such that the distance between the rasping surface and the guiding surface increases in the direction toward the outer free ends of the C-shaped body.

With such a trial rasp therefore the guiding surface acts as a non-cutting guide along the precut posterior surface of the femur, and the precut posterior surface of the bone slides easily relative to it, so giving accurate ultimate alignment. In addition, the rasping surface prepares what is the largest single surface of the cut bone on the anterior to permit a tight interference fit suitable for bone ingrowth to occur. Also, because the trial rasp according to the invention slides accurately over the end of the bone without skewing around or producing the "see-saw" effect, the accurate final positioning of the femoral trial will optimize bone cut in all cut regions of the condyles. Medio lateral alignment is ensured by the eye to give central location.

Once the femoral trial is in place and satisfactory articulation has been obtained in a trial reduction, the condylar alignment holes may be drilled to receive the alignment pegs of the implant proper. Thereafter, the femoral trial is removed and the implant itself fixed finally in place.

Other features will be pointed out hereinafter.

BRIEF DESCRIPTION OF THE DRAWING

The invention will be further described by way of example with reference to the drawing wherein corresponding reference characters indicate corresponding parts throughout the several views of the drawing, and wherein.

DETAILED DESCRIPTION OF PREFERRED EMBODIMENTS

1. Impactor/Extractor Holder

Figures 1, 2:
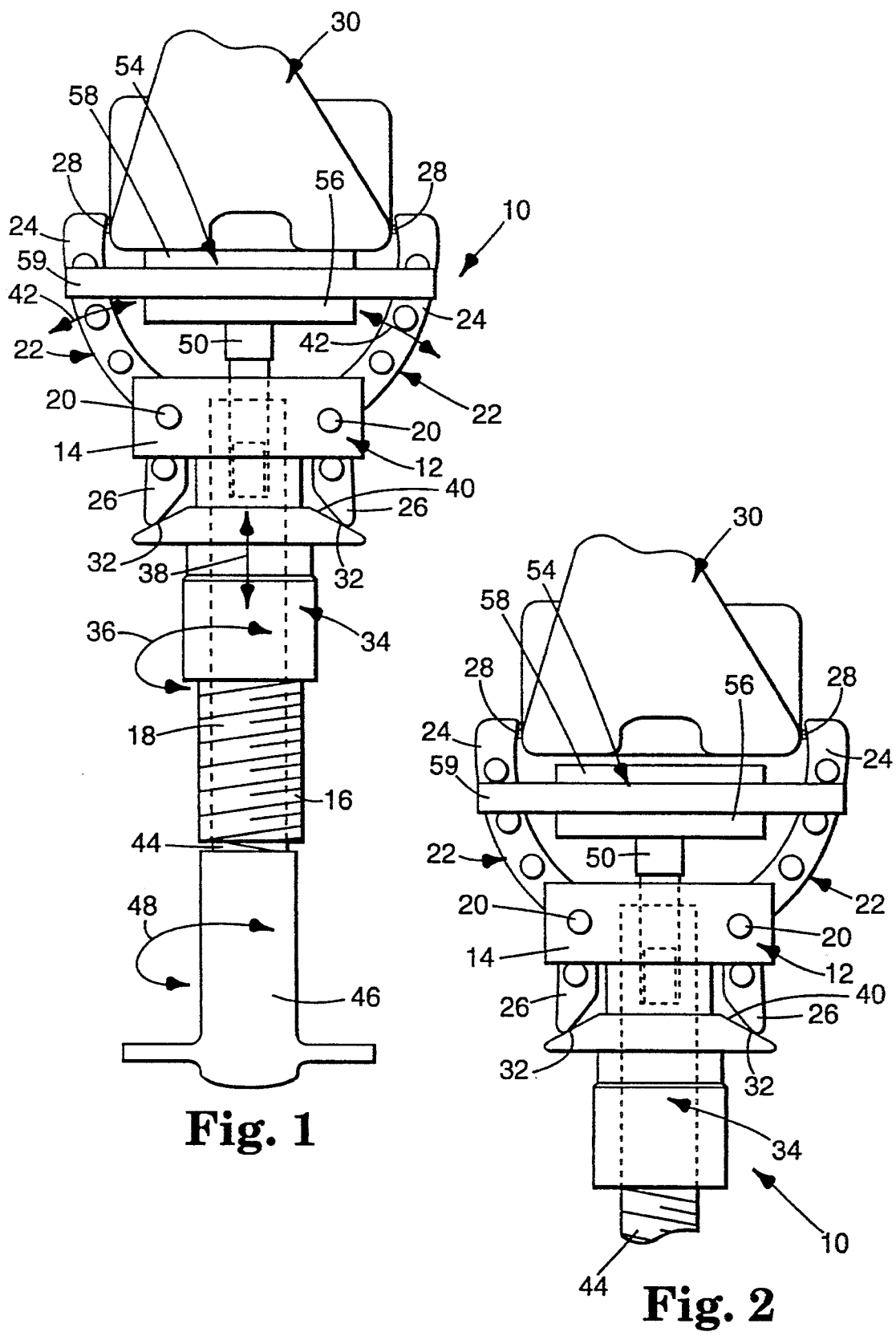
FIG. 1 is a front view of an impactor/extractor holder according to the invention shown gripping an implant or trial.
FIG. 2 is a detail similar to FIG. 1 but showing the table retracted.

The impactor/extractor holder 10 shown in the drawings includes a generally elongate main body 12. The main body 12 is somewhat T-shaped including a cross piece 14, and an elongate sleeve 16 whose outwardly facing surface has a screw-thread 18.

Pivoted to the cross piece 14 about pivot pins 20 defining fulcra, are a pair of two-armed levers 22 constituting clamping jaws 22. Each lever 22 includes a clamping arm 24 extending in one direction from its fulcrum 20, and an actuating arm 26 extending in the other direction from the clamping arm 24 at the fulcrum 20. The arrangement is such that, when the actuating arms 26 are moved outwardly relative to the main body 12 of the impactor/extractor holder 10, the clamping arms 24 are moved toward one another to clamp the opposite outer edges of the trial or implant. At the ends of the actuating arms 26 are beveled actuating surfaces 32.

At the ends of the clamping arms 24 are small locking projections 28 having generally rectangular cross sections, which are arranged to engage and fit corresponding shaped opposed recesses in the opposite outer edges of a trial or implant 30. The opposite outer edges of the trial or implant 30 constitute the outer medial and lateral sides of the trial or implant 30. The projections 28 generally extend inwardly toward one another to be received in the recesses of the trial or implant 30.

Most preferably, the clamping jaws 22 are formed of stainless steel, and the clamping arms 24 are preferably arcuate, with the concave side facing inwardly toward the other clamping arm 24.

Mounted over the sleeve 16 of the main body 12 is a rotatable member 34. The rotatable member 34 is of generally conical or frustoconical shape, and has an internal screw thread which mates with the thread 18 of the sleeve 16 of the main body 12. The rotatable member 34 has a frustoconical-shaped outer surface 40 which engages with the actuating surface 32 on the actuating arms 26. The rotatable member 34 constitutes one preferred embodiment of the means for moving the clamping jaws 22 relative to one another and adjustably maintaining the clamping jaws 22 against relative outward movement.

Figure 3:
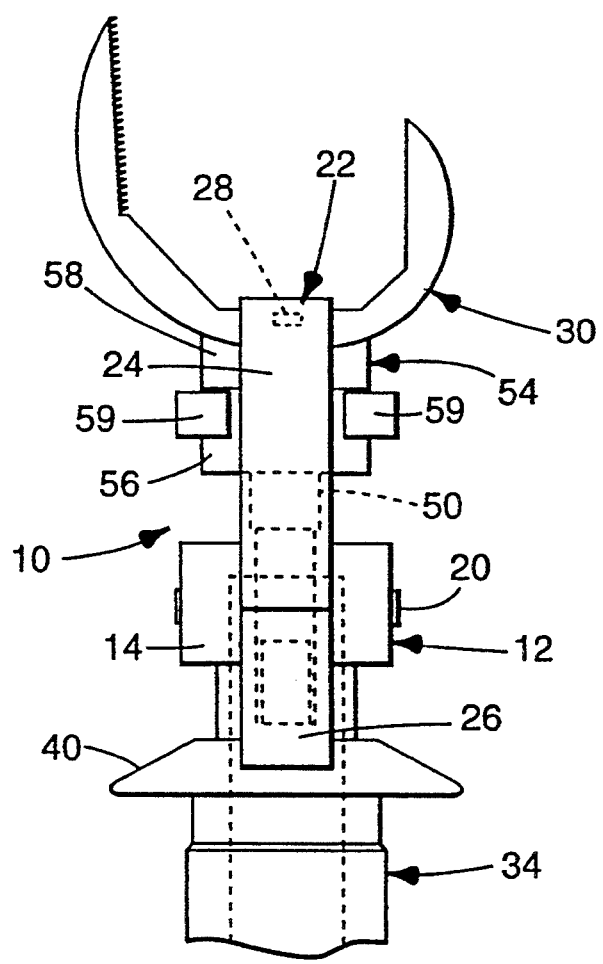
FIG. 3 is a side view detail of the holder.

When the rotatable member 34 is twisted in the direction of one of the arrows 36 relative the sleeve 16, the rotatable member 34 will move axially along the sleeve 16 in the direction of one of the arrows 38. That is, when the rotatable member 36 is twisted in one direction, the rotatable member 34 moves in the direction upwardly in FIGS. 1–3 to drive the actuating arms 26 of the clamping jaws 22 apart, thereby bringing the clamping arms 24 together to grip the trial or implant 30. When the rotatable member 34 is twisted in the other direction, the rotatable member 34 moves in the direction downwardly in FIGS. 1–3 to allow the actuating arms 26 of the clamping jaws 22 to move toward each other, thereby allowing the clamping arms 24 to move away from one another, for example, to release an implant or trial 30.

The sleeve 16 of the main body 12 also has an internal screw thread (not shown), and threaded into this is an externally screwed threaded shaft 44. This shaft 44 is fixed at one end to a handle 46 to assist in twisting the shaft 44 relative the sleeve 16 in the direction of the arrows 48. At its other end the shaft 44 is fixed via a swivel joint 50 to an abutment table 54. The shaft 44 and handle 46 facilitate moving the abutment table 54 relative to the clamping arms 24. The abutment table 54 is connected to the threaded shaft 44 by the swivel joint 50 such that the shaft 44 may be rotated to move the abutment table 54 in the direction of elongation of the sleeve 16 of the main body 12 without rotating the abutment table 54.

The abutment table 54 includes a metal backing plate 56 faced with a sheet 58 of a synthetic plastics material such as available under the trademark "TUFNOL" from Tufnol Limited, Birmingham, England. The sheet 58 provides a cushioning surface (also 58) which is arranged to contact the highly-polished, curved, outer, articulation surface of the implant 30. The material of the sheet 58 was selected so that when the sheet 58 contacts the trial or implant 30, and in the particular case of the implant 30, it will not harm the highly polished articulating surfaces of the implant 30.

In addition, the plate 56 of the abutment table 54 has a pair of extensions 59, which embrace the clamping arms 24 to prevent significant rotation of the abutment table 54 relative to the main body 12 while allowing movement of the abutment table 54 in the direction of elongation of the sleeve 16 of the main body 12. There is some freedom of swivelling movement to allow the abutment table 54 to adjust into contact with the implant or trial 30 as will be described, because the gap between the extensions is greater than the width of the arms 24 (see FIG. 3). However, the extensions 59 prevent rotation of the table 54 when the rod 44 is twisted.

When the handle 46 and rod 44 are twisted to advance the table 54 towards the trial or implant, the surface 58 will abut the trial or implant 30 and, together with the grip by the clamping arms 24, will rigidly secure the impactor/extractor holder 10 to it. As a result, the trial or implant 30 can be handled and located and if necessary hammered into place by hammering on the end of the handle 46. In that connection it is notable that the hammering effect can be transmitted directly through the rod 44 to the table 54 and to the trial or implant 30.

The mechanical advantage of the clamping arrangement (clamping arms 22 and abutment table 54) is such as to ensure that the back pressure from locking the clamping arms 22 and abutment table 54 in place is sufficient to prevent loosening of the grip during manoeuvering of the trial or implant 30 or 130.

In operation of the impactor/extractor holder 10, movement of the clamping jaws 22 by twisting rotatable member 34 and movement of the abutment table 54 by twisting handle 46 permit adjustment of the holder 10 to securely and rigidly hold a range of sizes of implants and/or trials 30. The impactor/extractor holder 10 facilitates positioning and manipulating the femoral component, femoral trial or trial rasp 30 or 130 by providing a holder 10 that may be manually grasped to force the femoral component, femoral trial or trial rasp 30 or 130 over the precut end of the femur, and to remove the femoral trial or trial rasp, or the femoral component if necessary, from the distal, precut end of the femur.

2. Trial Rasp

Figure 7:
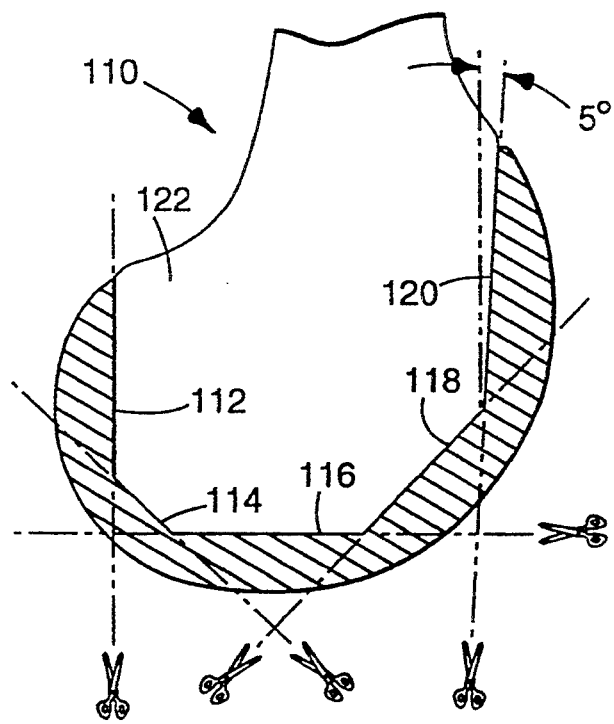
FIG. 7 is a view of the distal end of a femur showing the cuts which are made to remove bone.

In the preparation of the distal femur to receive an artificial knee joint, it is first of all necessary to cut the condyles to a shape and size to fit tightly with the implant. FIG. 7 shows the distal end 110 of a femur and the five cuts 112 to 120 which can be made, the portions of bone being removed being shown cross hatched.

The cut 116 is made so as to be at right angles to the mechanical axis of the leg through the knee. The posterior cut 112 is made at right angles to the cut 116, whilst the anterior cut 120 is at an angle of about 5° to the posterior cut, so that the resected condyle 122 tapers slightly in a direction towards the knee. Lastly the cuts 114 and 118 are at 45° to the cut 116 and, as can be seen from FIG. 7, the use of five cuts in this way removes a roughly equal thickness of bone around the articulation surface of the condyles and ultimately corresponds to the section of the implanted knee joint.

The various cuts are usually made using a mitre guide block. For example, the mitre block (not shown) may be as described in coassigned British Patent Application Serial No. 9213766.0, hereby incorporated by reference. However, the cut 120 is made such that the width of the resected condyles is slightly large, e.g. of the order of 0.1 to 0.5 mm too large, for reasons which will be described.

Figure 4:
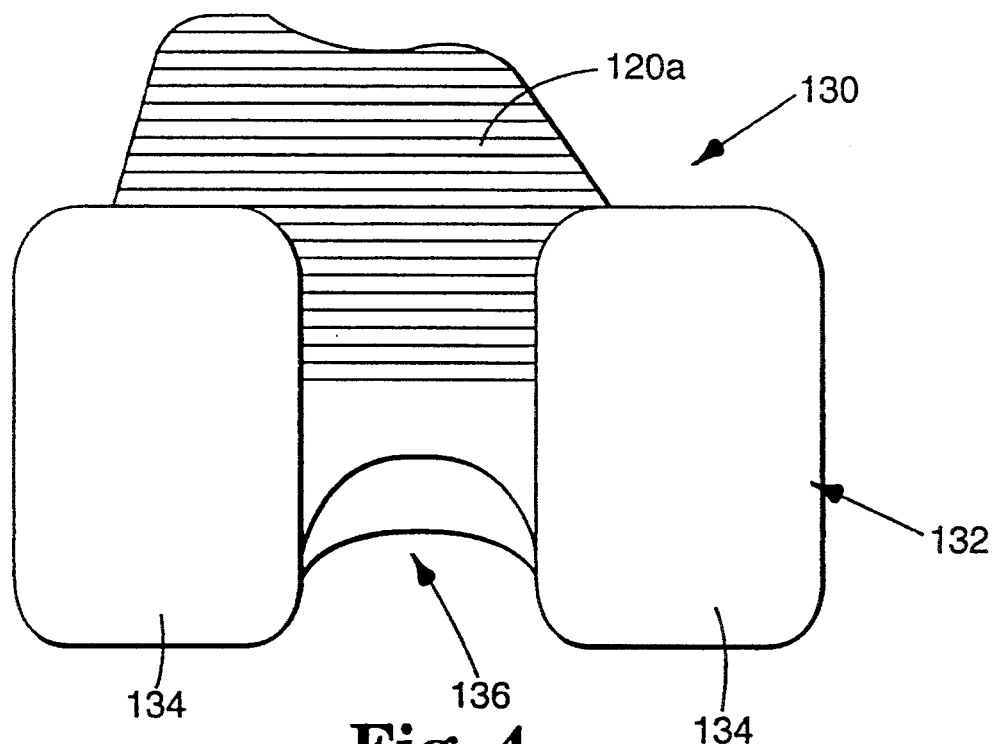
FIG. 4 is a posterior view of a trial rasp according to the invention.
Figure 5:
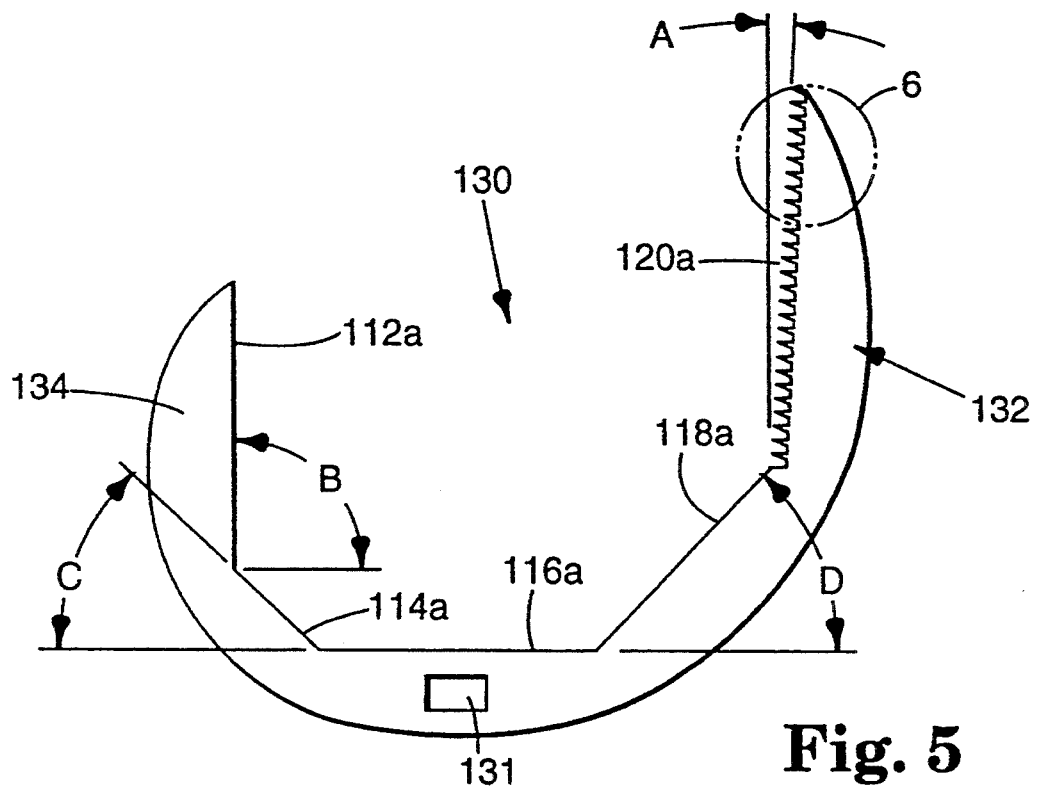
FIG. 5 is a side view of the trial rasp.
Figure 6:
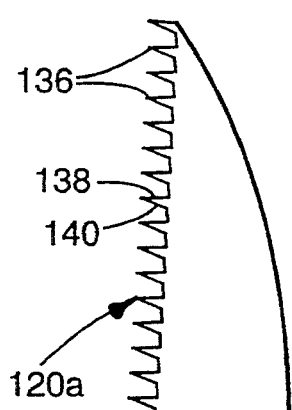
FIG. 6 is an enlarged sectional detailed view of the area within the circle marked 6 in FIG. 5.

A trial rasp 130 according to the invention is best shown in FIGS. 4 to 6. The trial rasp 130 constitutes one alternative embodiment of the femoral trial 30 that may be held with the impactor/extractor holder 10 described above. In this regard, two opposed recesses 131 (FIG. 5) having generally rectangular cross section are preferably provided in the opposite medial/lateral outer edges of the trial rasp 130. It will be appreciated that the trial rasp 130 may also be used with other types of holders 10, although the holder 10 is preferred.

The trial rasp 130 comprises a metal body 132 of a shape and size corresponding to the final implant. It has a hollow, generally "C" shaped body (also 132) having a concave or inner side capable of being received over the end of the femur which has been prepared (precut) to receive the femoral component. The concave side of the rasp 130 is provided with surfaces 112a to 120a corresponding to the cuts 112 to 120, respectively, which have been made in the condyles. The trial rasp 130 has a curved outer surface corresponding to the articulating surface of the femur and equally the final articulation surface of the implant.

Two planar guiding surfaces 112a are provided along one end portion (also 112a) of the concave side of the trial rasp 130. One of the two posterior guiding surfaces 112a is provided in each of a pair of legs 134, with a gap 136 between these legs 134 corresponding to the ligamental groove between the condyles known as the "Incisura Intercondylica". The guiding surfaces 112a are plain, that is, they do not have any rasping teeth and they are relatively smooth in comparison to the rasping surface 120a. As used herein, "smooth" means sufficiently smooth as not to be used to rasp or cut bone.

By contrast the rasping surface 120a is provided with parallel rows of closely-spaced rasping teeth 136. As best seen from FIG. 6, each tooth has a leading cutting face 138 approximately at right angle to the surfaces 120a and an inclined trailing face 140. The rasping teeth 136 are preferably arranged along the rasping surface 120a parallel to one another and extending in the direction substantially transverse to the direction that the trial rasp 130 is forced over the bone. Alternatively, the parallel rasping teeth could be provided at an angle other than 90 degrees to the direction in which the trial rasp is inserted over the bone.

The rasping teeth 136 are preferably adapted so as to remove only a very small amount of bone, for example, 0.1-2 mm, most preferably 0.1-0.5 mm. The cuts which are made in the end of the femur will therefore need to be accurate to at least that size, and the anterior cut is designed to leave the condyles that much larger than the final required size.

The rasping surface 120a is generally opposed to the guiding surface 112a along the other end portion (also 120a) of the C-shaped body. The rasping surface 120a is adapted to contact the precut anterior surface 120b (FIG. 8) of the femur. The rasping surface 120a is adapted to rasp the precut anterior surface 120b of the femur as the trial rasp 130 is advanced over the distal end 110 of the femur while the guiding surfaces 112a engage the posterior precut surface 112b of the femur to guide the rasping surface 120a in proper alignment relative to the femur.

Preferably, the rasping surface 120a is not parallel to the guiding surfaces 112a, but is instead offset by a small angle, most preferably, approximately 5 degrees. The C-shaped body 132 has outer ends between which the femur is received along the concave side of the C-shaped body 132. The rasping surface 120a is most preferably oriented at the angle relative to the guiding surfaces 112a such that the distance between the rasping surface 120a and the guiding surfaces 112a increases in the direction toward the outer free ends of the C-shaped body 132.

Once the cuts 112 to 120 have been made, the trial rasp 130 is forced over the resected end 122 of the femur. This can, for example, be assisted by using the impactor/extractor holder 10 as described above.

Figure 8:
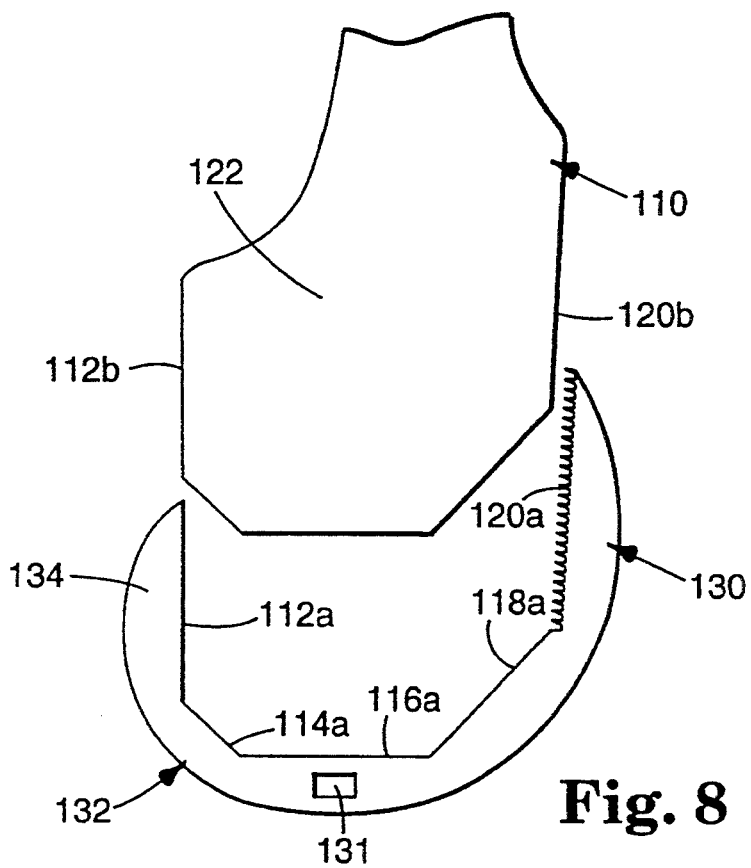
FIG. 8 is a view showing the resected femoral condyle with the trial rasp being inserted over it.

As best shown in FIG. 8, as the trial rasp 130 is forced over the end of the femur, the posterior cut surface 112b abuts the plain posterior surfaces 112a and slides relative to them to act as a guide. Meanwhile the anterior cut surface 120b progressively contacts the rasping surface 120a and slight shaving of the bone occurs to remove sufficient bone to give an interference fit between the various cut surfaces of the bone and the surfaces 112a to 120a.

Once the surgeon has finished tests with the trial rasp 130, this is removed and the final implant fitted in the normal way.

As various changes could be made in the above constructions and methods without departing from the scope of the invention, it is intended that all matter contained in the above description or shown in the accompanying drawing shall be interpreted as illustrative and not in a limiting sense.

We claim:

1. An impactor/extractor holder for a femoral trial or a femoral condylar knee implant to hold and guide one of the femoral trial and knee implant onto the resected end of a femur, the trial or implant having opposite outer edges and an outer surface, the impactor/extractor holder comprising:

two opposed clamping jaws having opposed locking projections that are movable toward one another to press inwardly against the opposite outer edges of the trial or implant, the locking projections of the clamping jaws facing in the direction generally toward one another to grip the opposite outer edges of the trial or implant;

means for moving the clamping jaws relative to one another and adjustably maintaining the clamping jaws against relative outward movement;

an abutment table mounted between the clamping jaws for movement relative to the clamping jaws so as to be capable of being advanced against the outer surface of the trial or implant after the sides have been clamped by the clamping jaws, the abutment table having a cushioning surface for contacting the trial or implant which will not damage the outer surface of the implant or trial, the cushioning surface being formed of plastic material; and means for moving the abutment table relative to the clamping jaws to advance the cushioning surface of the abutment table against the outer surface of the implant or the trial to press the trial or implant toward the locking projections of the clamping jaws to securely and rigidly lock the trial or implant between the abutment table and the two opposed clamping jaws;

the means for moving being rotatable relative to the abutment table.

2. An impactor/extractor holder according to claim 1 in which both the clamping jaws and abutment table are adjustable to hold a range of sizes of implants and/or trials.

3. An impactor/extractor holder for a femoral trial or a knee implant to hold and guide one of the femoral trial and knee implant onto the resected end of a femur, the trial or implant having opposite outer edges and an outer surface, the impactor/extractor holder comprising:

two opposed clamping jaws movable toward one another for gripping the opposite outer edges of the trial or implant;

means for moving the clamping jaws relative to one another and adjustably maintaining the clamping jaws against relative outward movement;

an abutment table mounted between the clamping jaws for movement relative to the clamping jaws so as to be capable of being advanced against the outer surface of the trial or implant after the sides have been clamped by the clamping jaws, the abutment table having a cushioning surface for contacting the trial or implant which will not damage the outer surface of the implant or trial; and means for moving the abutment table relative to the clamping jaws to advance the cushioning surface of the abutment table against the outer surface of the implant or the trial to securely and rigidly lock the trial or implant between the abutment table and the two opposed clamping jaws;

both the clamping jaws and abutment table being adjustable to hold a range of sizes of implants and/or trials;

the means for moving the clamping jaws relative to one another and adjustably maintaining the clamping jaws against relative outward movement comprising first threaded adjustment means for moving the clamping jaws to grip the opposite edges of the trial or implant; and the means for moving the abutment table comprising second threaded adjustment means for adjustably moving the cushioning surface of the abutment table relative to the clamping jaws to securely and rigidly lock the implant or trial on the holder.

4. An impactor/extractor holder according to claim 3 adapted for holding a trial or implant having opposed recesses in the opposite edges; the clamping jaws including locking projections sized and shaped to locate into opposed recesses on the trial and/or implant.

5. An impactor/extractor holder according to claim 4 adapted for holding a trial or implant having opposed recesses of generally rectangular cross section; the locking projections having a generally rectangular cross section.

6. An impactor/extractor holder according to claim 4 comprising a main body having fulcra for the clamping jaws;

the clamping jaws comprising a pair of opposed two-armed levers pivotably mounted on the fulcra on the main body, each lever comprising a clamping jaw extending in one direction from its respective fulcrum, and an actuating jaw extending from its respective clamping arm in the other direction from its respective fulcrum such that, when the actuating arms are moved outwardly relative to the main body of the holder, the clamping jaws are moved toward one another to clamp the opposite edges of the trial or implant;

the first threaded adjustment means including means for moving the actuating arms of the levers outwardly, thereby moving the clamping jaws toward one another to clamp the opposite edges of the trial or implant.

7. An impactor/extractor holder according to claim 6 wherein the main body is generally elongate;

the first threaded adjustment means comprising a rotatable member threadably mounted on the main body for rotation relative to the main body to move the rotatable member longitudinally along the main body; and the means for moving the actuating arms of the levers outwardly comprising a surface on the rotatable member that engages the actuating arms of the levers to move the actuating arms outwardly as the rotatable member is advanced along the main body in one direction, the surface of the rotatable member allowing the actuating arms to move toward one another, thereby allowing the clamping jaws to move apart, when the rotatable member is moved in the other direction along the main body.

8. An impactor/extractor holder according to claim 7 wherein the surface of the rotatable member is generally conical or frustoconical.

9. An impactor/extractor holder according to claim 7 wherein the main body has opposite ends, an outside threaded surface, and an inside threaded bore extending between its ends, the abutment table and clamping jaws being adjacent one end of the main body;

the rotatable member being threadably mounted on the outside threaded surface of the main body;

the second threaded adjustment means including a handle, adjacent the end of the main body opposite the clamping jaws and abutment table; and a threaded shaft threadably received in the inside threaded bore of the main body, with one end of the threaded shaft having the handle mounted thereon and the other end of the threaded shaft being connected to the abutment table to move the abutment table relative to the clamping jaws.

10. An impactor/extractor holder according to claim 9 wherein the abutment table is so mounted on the main body as to allow movement in the direction of elongation of the main body without allowing rotation of the abutment table relative to the main body, the abutment table being so connected to the threaded shaft of the second threaded adjustment means as to move the abutment table in the direction of elongation of the main body without rotating the abutment table;

the abutment table including a rigid support for the cushioning surface, the cushioning surface being formed of synthetic plastics material arranged to contact the implant or trial.

11. An impactor/extractor holder according to claim 3 comprising a main body having fulcra for the clamping jaws;

the clamping jaws comprising a pair of opposed two-armed levers pivotably mounted on the fulcra on the main body, each lever comprising a clamping jaw extending in one direction from its respective fulcrum, and an actuating jaw extending from its respective clamping arm in the other direction from its respective fulcrum such that, when the actuating jaws are moved outwardly relative to the main body of the holder, the clamping arms are moved toward one another to clamp the opposite edges of the trial or implant;

the first threaded adjustment means including means for moving the actuating jaws of the levers outwardly, thereby moving the clamping arms toward one another to clamp the opposite edges of the trial or implant.

12. An impactor/extractor holder according to claim 11 wherein the main body is generally elongate;

the first threaded adjustment means comprising a rotatable member threadably mounted on the main body for rotation relative to the main body to move the rotatable member longitudinally along the main body; and the means for moving the actuating arms of the levers outwardly comprising a surface on the rotatable member that engages the actuating arms of the levers to move the actuating arms outwardly as the rotatable member is advanced along the main body in one direction, the surface of the rotatable member allowing the actuating arms to move toward one another, thereby allowing the clamping jaws to move apart, when the rotatable member is moved in the other direction along the main body.

13. An impactor/extractor holder according to claim 12 wherein the surface of the rotatable member is generally conical or frustoconical.

14. An impactor/extractor holder according to claim 12 wherein the main body has opposite ends, an outside threaded surface, and an inside threaded bore extending between its ends, the abutment table and clamping jaws being adjacent one end of the main body;

the rotatable member being threadably mounted on the outside threaded surface of the main body;

the second threaded adjustment means including a handle, adjacent the end of the main body opposite the clamping jaws and abutment table; and a threaded shaft threadably received in the inside threaded bore of the main body, with one end of the threaded shaft having the handle mounted thereon and the other end of the threaded shaft being connected to the abutment table to move the abutment table relative to the clamping jaws.

15. An impactor/extractor holder according to claim 14 wherein the abutment table is so mounted on the main body as to allow movement in the direction of elongation of the main body without allowing rotation of the abutment table relative to the main body, the abutment table being so connected to the threaded shaft of the second threaded adjustment means as to move the abutment table in the direction of elongation of the main body without rotating the abutment table;

the abutment table including a rigid support for the cushioning surface, the cushioning surface being formed of synthetic plastics material arranged to contact the implant or trial.

16. The combination of a femoral trial for a femoral condylar implant and an impactor/extractor holder for the femoral trial to hold and guide the femoral trial onto the resected end of a femur;

the femoral trial having opposite outer edges corresponding to the outer medial and lateral edges of a femoral knee implant, and an outer surface;

the impactor/extractor holder comprising:

two opposed clamping jaws having opposed locking projections that are movable toward one another to press inwardly against the opposite outer edges of the femoral trial, the locking projections of the clamping jaws facing in the direction generally toward one another to grip the opposite outer edges of the femoral trial;

means for moving the clamping jaws relative to one another and adjustably maintaining the clamping jaws against relative outward movement;

an abutment table mounted between the clamping jaws for movement relative to the clamping jaws so as to be capable of being advanced against the outer surface of the femoral trial after the opposite edges of the femoral trial have been clamped by the clamping jaws, the abutment table having a cushioning surface for contacting the outer surface of the femoral trial, the cushioning surface being formed of plastic material; and means for moving the abutment table relative to the clamping jaws to advance the cushioning surface of the abutment table against the outer surface of the femoral trial to press the trial toward the locking projections of the clamping jaws to securely and rigidly lock the femoral trial between the abutment table and the two opposed clamping jaws;

the abutment table being constrained from rotation relative to the clamping jaws as the abutment table is advanced by the means for moving the abutment table relative to the clamping jaws.

17. The combination according to claim 16 further comprising a range of sizes of femoral trials corresponding to a range in sizes of femoral components of artificial knee implants, both the clamping jaws and abutment table being adjustable to hold the range of sizes of trials.

18. The combination of a femoral trial corresponding in size of femoral component to a an artificial knee implant and an impactor/extractor holder for the femoral trial to hold and guide the femoral trial onto the resected end of a femur;

the femoral trial having opposite outer edges corresponding to the outer medial and lateral edges of a femoral knee implant, and an outer surface;

the impactor/extractor holder comprising:

two opposed clamping jaws movable toward one another for gripping the opposite outer edges of the femoral trial;

means for moving the clamping jaws relative to one another and adjustably maintaining the clamping jaws against relative outward movement;

an abutment table mounted between the clamping jaws for movement relative to the clamping jaws so as to be capable of being advanced against the outer surface of the femoral trial after the opposite edges of the femoral trial have been clamped by the clamping jaws, the abutment table having a cushioning surface for contacting the outer surface of the femoral trial; and means for moving the abutment table relative to the clamping jaws to advance the cushioning surface of the abutment table against the outer surface of the femoral trial to securely and rigidly lock the femoral trial between the abutment table and the two opposed clamping jaws;

both the clamping jaws and abutment table being adjustable to hold different sizes of trials;

the means for moving the clamping jaws relative to one another and adjustably maintaining the clamping jaws against relative outward movement comprising first threaded adjustment means for moving the clamping jaws to grip the opposite outer edges of the trial; and the means for moving the abutment table comprising second threaded adjustment means for adjustably moving the cushioning surface of the abutment table relative to the clamping jaws to securely and rigidly lock the trial on the holder.

19. The combination according to claim 18 wherein the trial has opposed recesses in the opposite outer edges; the clamping jaws including locking projections sized and shaped to locate into opposed recesses on the trial and/or implant.

20. The combination according to claim 19 wherein the opposed recesses of the femoral trial have generally rectangular cross sections; the locking projections having a generally rectangular cross section.

21. The combination according to claim 19 wherein the impactor/extractor holder further comprises a generally elongate main body having fulcra for the clamping jaws;

the clamping jaws comprising a pair of opposed two-armed levers pivotably mounted on the fulcra on the main body, each lever comprising a clamping jaw extending in one direction from its respective fulcrum; and an actuating arm extending from its respective clamping jaw in the other direction from its respective fulcrum such that, when the actuating arms are moved outwardly relative to the main body of the holder, the clamping jaws are moved toward one another to clamp the opposite edges of the trial;

the first threaded adjustment means comprising:

a rotatable member threadably mounted on the main body for rotation relative to the main body to move the rotatable member longitudinally along the main body; and a surface on the rotatable member that engages the actuating arms of the levers to move the actuating arms outwardly as the rotatable member is advanced along the main body in one direction, the surface of the rotatable member allowing the actuating arms to move toward one another when the rotatable member is moved in the other direction along the main body.

22. The combination according to claim 21 wherein the surface of the rotatable member is generally conical or frustoconical.

23. The combination according to claim 21 wherein the main body has opposite ends, an outside threaded surface, and an inside threaded bore extending between its ends, the abutment table and clamping jaws being adjacent one end of the main body;

the rotatable member being threadably mounted on the outside threaded surface of the main body;

the second threaded adjustment means including a handle, adjacent the end of the main body opposite the clamping jaws and abutment table; and a threaded shaft threadably received in the inside threaded bore of the main body, with one end of the threaded shaft having the handle mounted thereon and the other end of the threaded shaft being connected to the abutment table to move the abutment table relative to the clamping jaws.

24. The combination according to claim 23 wherein the abutment table is so mounted on the main body as to allow movement in the direction of elongation of the main body without allowing rotation of the abutment table relative to the main body, the abutment table being so connected to the threaded shaft of the second threaded adjustment means as to move the abutment table in the direction of elongation of the main body without rotating the abutment table.

25. The combination according to claim 24 wherein the femoral trial comprises a trial rasp for preparing the femur for the femoral component of a knee joint prosthesis, the rasp comprising a generally C-shaped body having a concave side with opposite end portions capable of being received over the end of the femur which has been prepared to receive the femoral component, the concave side of the body having:
- a relatively smooth guiding surface along one end portion of the concave side of the C-shaped body, the guiding surface being adapted to contact a prepared posterior surface of the femur which has been cut in a direction substantially parallel to the axis of the femur to guide the rasp relative to the posterior surface of the femur; and
- a rasping surface generally opposed to the guiding surface along the other end portion of the concave side of the C-shaped body, the rasping surface being adapted to contact a prepared anterior surface of the femur, the rasping surface being adapted to rasp the prepared anterior surface of the femur as the trial rasp is advanced over the end of the femur while the guiding surfaces engages the prepared posterior surface to guide the rasping surface in proper alignment relative to the femur.

26. The combination according to claim 25 in which the rasping surface is in the form of a number of closely spaced cutting edges which are substantially parallel to one another and substantially transverse to the direction in which the rasp is forced over the bone.

27. The combination according to claim 25 in which the rasping surface is in the form of a number of closely spaced cutting edges which are substantially parallel to one another and which extend in at an angle other than 90° to the direction in which the trial rasp is inserted over the femur.

28. The combination according to claim 25 in which the rasping surface is not parallel to the guiding surface.

29. The combination according to claim 28 in which the C-shaped body has outer free ends between which the femur is received along the concave side of the body, the rasping surface being oriented at an angle relative to the guiding surface such that the distance between the rasping surface and the guiding surface increases in the direction toward the outer free ends of the C-shaped body.

30. The combination according to claim 18 wherein the impactor/extractor holder further comprises a generally elongate main body having fulcra for the clamping jaws;
- the clamping jaws comprising a pair of opposed two-armed levers pivotably mounted on the fulcra on the main body, each lever comprising a clamping jaw extending in one direction from its respective fulcrum; and an actuating arm extending from its respective clamping jaw in the other direction from its respective fulcrum such that, when the actuating arms are moved outwardly relative to the main body of the holder, the clamping jaws are moved toward one another to clamp the opposite edges of the trial;
- the first threaded adjustment means comprising:
- a rotatable member threadably mounted on the main body for rotation relative to the main body to move the rotatable member longitudinally along the main body; and
- a surface on the rotatable member that engages the actuating arms of the levers to move the actuating arms outwardly as the rotatable member is advanced along the main body in one direction, the surface of the rotatable member allowing the actuating arms to move toward one another when the rotatable member is moved in the other direction along the main body.

31. The combination according to claim 30 wherein the surface of the rotatable member is generally conical or frustoconical.

32. The combination according to claim 30 wherein the main body has opposite ends, an outside threaded surface, and an inside threaded bore extending between its ends, the abutment table and clamping jaws being adjacent one end of the main body;
- the rotatable member being threadably mounted on the outside threaded surface of the main body;
- the second threaded adjustment means including a handle, adjacent the end of the main body opposite the clamping jaws and abutment table; and a threaded shaft threadably received in the inside threaded bore of the main body, with one end of the threaded shaft having the handle mounted thereon and the other end of the threaded shaft being connected to the abutment table to move the abutment table relative to the clamping jaws.

33. The combination according to claim 32 wherein the abutment table is so mounted on the main body as to allow movement in the direction of elongation of the main body without allowing rotation of the abutment table relative to the main body, the abutment table being so connected to the threaded shaft of the second threaded adjustment means as to move the abutment table in the direction of elongation of the main body without rotating the abutment table.

34. The combination of a femoral condylar component of an artificial knee implant and an impactor/extractor holder for the femoral condylar component to hold and guide the femoral condylar component onto the resected end of a femur;
- the femoral condylar component having opposite outer edges constituting outer medial and lateral edges, and an outer surface having a polished articulation surface;
- the impactor/extractor holder comprising:
- clamping jaws having opposed locking projections that are movable toward one another to press inwardly against the opposite outer edges of the femoral condylar component, the locking projections of the clamping jaws facing the direction generally toward one another to grip the opposite outer edges of the femoral condylar component;
- means for moving the clamping jaws relative to one another and adjustably maintaining the clamping jaws against relative outward movement;
- an abutment table mounted between the clamping jaws for movement relative to the clamping jaws so as to be capable of being advanced against the articulation surface of the femoral component after the opposite outer edges thereof have been clamped by the clamping jaws, the abutment table having a cushioning surface for contacting the articulation surface of the femoral component, the cushioning surface being formed of plastic material; and
- means for moving the abutment table relative to the clamping jaws to advance the cushioning surface of the abutment table against the articulation surface of the femoral component to press the femoral condylar component toward the locking projections of the clamping jaws to securely and rigidly lock the femoral component between the abutment table and the two clamping jaws;
- the abutment table being constrained from rotation relative to the clamping jaws as the abutment table is advanced by the means for moving the abutment table relative to the clamping jaws.

35. The combination of a femoral component of selectable size of an artificial knee implant and an impactor/extractor holder for the femoral component to hold and guide the femoral component onto the resected end of a femur;

the femoral component having opposite outer edges constituting outer medial and lateral edges, and an outer surface having a polished articulation surface;

the impactor/extractor holder comprising:

clamping jaws movable toward one another for gripping the opposite outer edges of the femoral component;

means for moving the clamping jaws relative to one another and adjustably maintaining the clamping jaws against relative outward movement;

an abutment table mounted between the clamping jaws for movement relative to the clamping jaws so as to be capable of being advanced against the articulation surface of the femoral component after the opposite outer edges thereof have been clamped by the clamping jaws, the abutment table having a cushioning surface for contacting the articulation surface of the femoral component; and means for moving the abutment table relative to the clamping jaws to advance the cushioning surface of the abutment table against the articulation surface of the femoral component to securely and rigidly lock the femoral component between the abutment table and the two clamping jaws;

both the clamping jaws and abutment table being adjustable to hold different sizes of trials;

the means for moving the clamping jaws relative to one another and adjustably maintaining the clamping jaws against relative outward movement comprising first threaded adjustment means for moving the clamping jaws to grip the opposite outer edges of the femoral component;

the means for moving the abutment table comprising second threaded adjustment means for adjustably moving the cushioning surface of the abutment table relative to the clamping jaws to securely and rigidly lock the femoral component on the holder.

36. The combination according to claim 35 wherein the femoral component has opposed recesses in the opposite edges; the clamping jaws including locking projections sized and shaped to locate into opposed recesses on the femoral component.

37. The combination according to claim 36 wherein the opposed recesses of the femoral component have generally rectangular cross sections, and the locking projections have generally rectangular cross sections complementary to the rectangular cross sections of the recesses of the femoral component.

38. The combination according to claim 36 wherein the impactor/extractor holder further comprises a generally elongate main body having fulcra for the clamping jaws;

the clamping jaws further comprising a pair of opposed two-armed levers pivotably mounted on the fulcra on the main body, each lever comprising a clamping jaw extending in one direction from its respective fulcrum; and an actuating arm extending from its respective clamping jaw in the other direction from its respective fulcrum such that, when the actuating arms are moved outwardly relative to the main body of the holder, the clamping jaws are moved toward one another to clamp the opposite edges of the femoral component;

the first threaded adjustment means comprising:

a rotatable member threadably mounted on the main body for rotation relative to the main body to move the rotatable member longitudinally along the main body; and a generally conical or frustoconical surface on the rotatable member that engages the actuating arms of the levers to move the actuating arms outwardly as the rotatable member is advanced along the main body in one direction, the surface of the rotatable member allowing the actuating arms to move toward one another when the rotatable member is moved in the other direction along the main body.

39. The combination according to claim 38 wherein the main body has opposite ends, an outside threaded surface, and an inside threaded bore extending between its ends, the abutment table and clamping jaws being adjacent one end of the main body;

the rotatable member being threadably mounted on the outside threaded surface of the main body;

the second threaded adjustment means including a handle, adjacent the end of the main body opposite the clamping jaws and abutment table; and a threaded shaft threadably received in the inside threaded bore of the main body, with one end of the threaded shaft having the handle mounted thereon and the other end of the threaded shaft being connected to the abutment table to move the abutment table relative to the clamping jaws; and the abutment table being so mounted on the main body as to allow movement in the direction of elongation of the main body without allowing rotation of the abutment table relative to the main body, the abutment table being so connected to the threaded shaft of the second threaded adjustment means as to move the abutment table in the direction of elongation of the main body without rotating the abutment table.

40. The combination according to claim 35 wherein the impactor/extractor holder further comprises a generally elongate main body having fulcra for the clamping jaws;

the clamping jaws further comprising a pair of opposed two-armed levers pivotably mounted on the fulcra on the main body, each lever comprising a clamping jaw extending in one direction from its respective fulcrum; and an actuating arm extending from its respective clamping jaw in the other direction from its respective fulcrum such that, when the actuating arms are moved outwardly relative to the main body of the holder, the clamping jaws are moved toward one another to clamp the opposite edges of the femoral component;

the first threaded adjustment means comprising:

a rotatable member threadably mounted on the main body for rotation relative to the main body to move the rotatable member longitudinally along the main body; and a generally conical or frustoconical surface on the rotatable member that engages the actuating arms of the levers to move the actuating arms outwardly as the rotatable member is advanced along the main body in one direction, the surface of the rotatable member allowing the actuating arms to move toward one another when the rotatable member is moved in the other direction along the main body.

41. The combination according to claim 40 wherein the main body has opposite ends, an outside threaded surface, and an inside threaded bore extending between its ends, the abutment table and clamping jaws being adjacent one end of the main body;

the rotatable member being threadably mounted on the outside threaded surface of the main body;

the second threaded adjustment means including a handle, adjacent the end of the main body opposite the clamping jaws and abutment table; and a threaded shaft threadably received in the inside threaded bore of the main body, with one end of the threaded shaft having the handle mounted thereon and the other end of the threaded shaft being connected to the abutment table to move the abutment table relative to the clamping jaws; and the abutment table being so mounted on the main body as to allow movement in the direction of elongation of the main body without allowing rotation of the abutment table relative to the main body, the abutment table being so connected to the threaded shaft of the second threaded adjustment means as to move the abutment table in the direction of elongation of the main body without rotating the abutment table.

* * * * *

UNITED STATES PATENT AND TRADEMARK OFFICE
CERTIFICATE OF CORRECTION

PATENT NO. : 5,417,693

DATED : May 23, 1995

INVENTOR(S) : Bjorn K. Sowden and John Egan

It is certified that error appears in the above-indentified patent and that said Letters Patent is hereby corrected as shown below:

Col. 10, line 54, "jaw" should read --arm--.
Col. 10, line 55, "jaw" should read --arm--.
Col. 10, line 59, "jaws" should read --arms--.
Col. 10, line 64, "jaws" should read --arms--.
Col. 11, line 13, "jaws" should read --arms--.
Col. 11, line 22, "jaws" should read --arms--.
Col. 11, line 28, "jaws" should read --arms--.
Col. 11, line 34, "jaws" should read --arms--.
Col. 11, line 54, "jaw" should read --arm--.
Col. 11, line 55, "jaw" should read --arm--.
Col. 11, line 58, "jaws" should read --arms--.
Col. 11, line 63, "jaws" should read --arms--.
Col. 12, line 13, "jaws" should read --arms--.
Col. 12, line 22, "jaws" should read --arms--.
Col. 12, line 28, "jaws" should read --arms--.
Col. 12, line 34, "jaws" should read --arms--.
Col. 13, line 24, "of" should read --to a--.
Col. 13, line 24, "to a" should read --of--.
Col. 14, line 14, "jaw" should read --arm--.
Col. 14, line 16, "jaw" should read --arm--.
Col. 14, line 19, "jaws" should read --arms--.

UNITED STATES PATENT AND TRADEMARK OFFICE
CERTIFICATE OF CORRECTION

PATENT NO. : 5,417,693
DATED : May 23, 1995
INVENTOR(S) : Bjorn K. Sowden and John Egan It is certified that error appears in the above-indentified patent and that said Letters Patent is hereby corrected as shown below:

Col. 14, line 41, "jaws" should read --arms--.
Col. 14, line 47, "jaws" should read --arms--.
Col. 14, line 53, "jaws" should read --arms--.
Col. 14, line 63, "24" should read --18--.
Col. 15, line 48, "jaw" should read --arm--.
Col. 15, line 50, "jaw" should read --arm--.
Col. 15, line 53, "jaws" should read --arms--.
Col. 16, line 7, "jaws" should read --arms--.
Col. 16, line 13, "jaws" should read --arms--.
Col. 16, line 19, "jaws" should read --arms--.
Col. 17, line 64, "jaw" should read --arm--.
Col. 17, line 66, "jaw" should read --arm--.
Col. 18, line 1, "jaws" should read --arms--.
Col. 18, line 20, "jaws" should read --arms--.
Col. 18, line 26, "jaws" should read --arms--.
Col. 18, line 33, "jaws" should read --arms--.
Col. 18, line 50, "jaw" should read --arm--.
Col. 18, line 52, "jaw" should read --arm--.
Col. 18, line 55, "jaws" should read --arms--.

UNITED STATES PATENT AND TRADEMARK OFFICE
CERTIFICATE OF CORRECTION

PATENT NO. : 5,417,693

DATED : May 23, 1995

INVENTOR(S) : Bjorn K. Sowden and John Egan

It is certified that error appears in the above-indentified patent and that said Letters Patent is hereby corrected as shown below:

Col. 19, line 6, "jaws" should read --arms--.

Col. 19, line 12, "jaws" should read --arms--.

Col. 20, line 4, "jaws" should read --arms--.

Signed and Sealed this

Twenty-second Day of October, 1996

*Attest:*

BRUCE LEHMAN

*Attesting Officer*     *Commissioner of Patents and Trademarks*